United States Patent
Hernandez et al.

(10) Patent No.: US 8,714,158 B2
(45) Date of Patent: May 6, 2014

(54) APPARATUS AND METHOD FOR CUSHIONING A VENTILATION MASK

(75) Inventors: Johnny Hernandez, Coral Springs, FL (US); Jerry Wright, Coconut Creek, FL (US); Rizwana Ahmed, Pembroke Pines, FL (US)

(73) Assignee: JRJ Medical Innovations, LLC, Coral Springs, FL (US)

( * ) Notice: Subject to any disclaimer, the term of this patent is extended or adjusted under 35 U.S.C. 154(b) by 780 days.

(21) Appl. No.: 12/400,539

(22) Filed: Mar. 9, 2009

(65) Prior Publication Data

US 2009/0223522 A1    Sep. 10, 2009

Related U.S. Application Data

(60) Provisional application No. 61/034,597, filed on Mar. 7, 2008.

(51) Int. Cl.
*A62B 18/08* (2006.01)

(52) U.S. Cl.
USPC .................................................. 128/206.24

(58) Field of Classification Search
USPC ............. 128/200.24, 206.24, 207.18, 206.23, 128/207.13, 206.27, 202.27, 206.21, 128/206.22, 206.25, 206.26, 206.28, 128/207.12, 207.11, 206.29, 201.22, 128/201.23, 201.24, 201.27, 857, 858, 128/202.18; 2/9, 206, 6.1, 6.2, 411, 424, 2/429, 446

See application file for complete search history.

(56) References Cited

U.S. PATENT DOCUMENTS

| | | | | |
|---|---|---|---|---|
| 4,153,051 | A * | 5/1979 | Shippert | 602/17 |
| 4,641,379 | A * | 2/1987 | Martin | 2/9 |
| 4,653,124 | A * | 3/1987 | McNeal et al. | 2/427 |
| 4,944,310 | A * | 7/1990 | Sullivan | 128/848 |
| 5,143,061 | A * | 9/1992 | Kaimer | 128/206.24 |
| 5,890,486 | A * | 4/1999 | Mitra et al. | 128/200.24 |
| 5,909,732 | A | 6/1999 | Diesel | |
| 6,082,360 | A * | 7/2000 | Rudolph et al. | 128/206.25 |
| 6,092,521 | A * | 7/2000 | Miura | 128/201.13 |
| 6,116,236 | A * | 9/2000 | Wyss | 128/200.24 |
| D434,879 | S * | 12/2000 | Cole | D29/122 |
| 6,328,038 | B1 * | 12/2001 | Kessler et al. | 128/207.18 |
| 7,077,140 | B1 * | 7/2006 | Berke | 128/206.25 |
| 7,152,601 | B2 * | 12/2006 | Barakat et al. | 128/206.14 |
| 7,210,481 | B1 * | 5/2007 | Lovell et | 128/205.25 |
| 7,243,650 | B2 * | 7/2007 | Thornton | 128/205.25 |
| 7,992,564 | B2 * | 8/2011 | Doshi et al. | 128/207.18 |
| 8,240,302 | B1 * | 8/2012 | Tayebi et al. | 128/201.15 |
| 2001/0022180 | A1 * | 9/2001 | Semeia | 128/201.27 |
| 2003/0056785 | A1 * | 3/2003 | Narihiko et al. | 128/201.26 |
| 2003/0136410 | A1 * | 7/2003 | Matich | 128/206.25 |
| 2006/0076019 | A1 | 4/2006 | Ho et al. | |
| 2007/0107735 | A1 | 5/2007 | Kwok et al. | |
| 2007/0125384 | A1 | 6/2007 | Zollinger et al. | |
| 2007/0125385 | A1 | 6/2007 | Ho et al. | |
| 2007/0163594 | A1 | 7/2007 | Ho et al. | |

(Continued)

*Primary Examiner* — Lynne Anderson
*Assistant Examiner* — Bradley Philips
(74) *Attorney, Agent, or Firm* — McClure, Qualey & Rodack, LLP

(57) ABSTRACT

Embodiments of apparatuses and methods for preventing facial wounds caused by an applied ventilation mask are provided. For example, the apparatus includes a cushion formed in an inverted "V" shape, wherein the cushion comprises a superior portion and two inferior portions, wherein the superior portion corresponds to the vertex of the inverted "V" shape, wherein the superior portion is configured to cushion the nose of a human, and wherein the two inferior portions are configured to cushion the cheekbones of a human.

17 Claims, 10 Drawing Sheets

PERSPECTIVE VIEW

(56) References Cited

U.S. PATENT DOCUMENTS

| | | | |
|---|---|---|---|
| 2008/0184995 A1* | 8/2008 | Ierulli | 128/200.24 |
| 2008/0302365 A1* | 12/2008 | Cohen et al. | 128/206.12 |
| 2009/0020115 A1* | 1/2009 | Lockwood, Jr. | 128/200.24 |
| 2010/0000534 A1* | 1/2010 | Kooij et al. | 128/204.18 |
| 2010/0018535 A1* | 1/2010 | Chimenti et al. | 128/206.24 |
| 2011/0239347 A1* | 10/2011 | Beliveau | 2/9 |
| 2011/0315146 A1* | 12/2011 | Beevers et al. | 128/207.13 |
| 2012/0067350 A1* | 3/2012 | Palmer, Jr. | 128/207.13 |

* cited by examiner

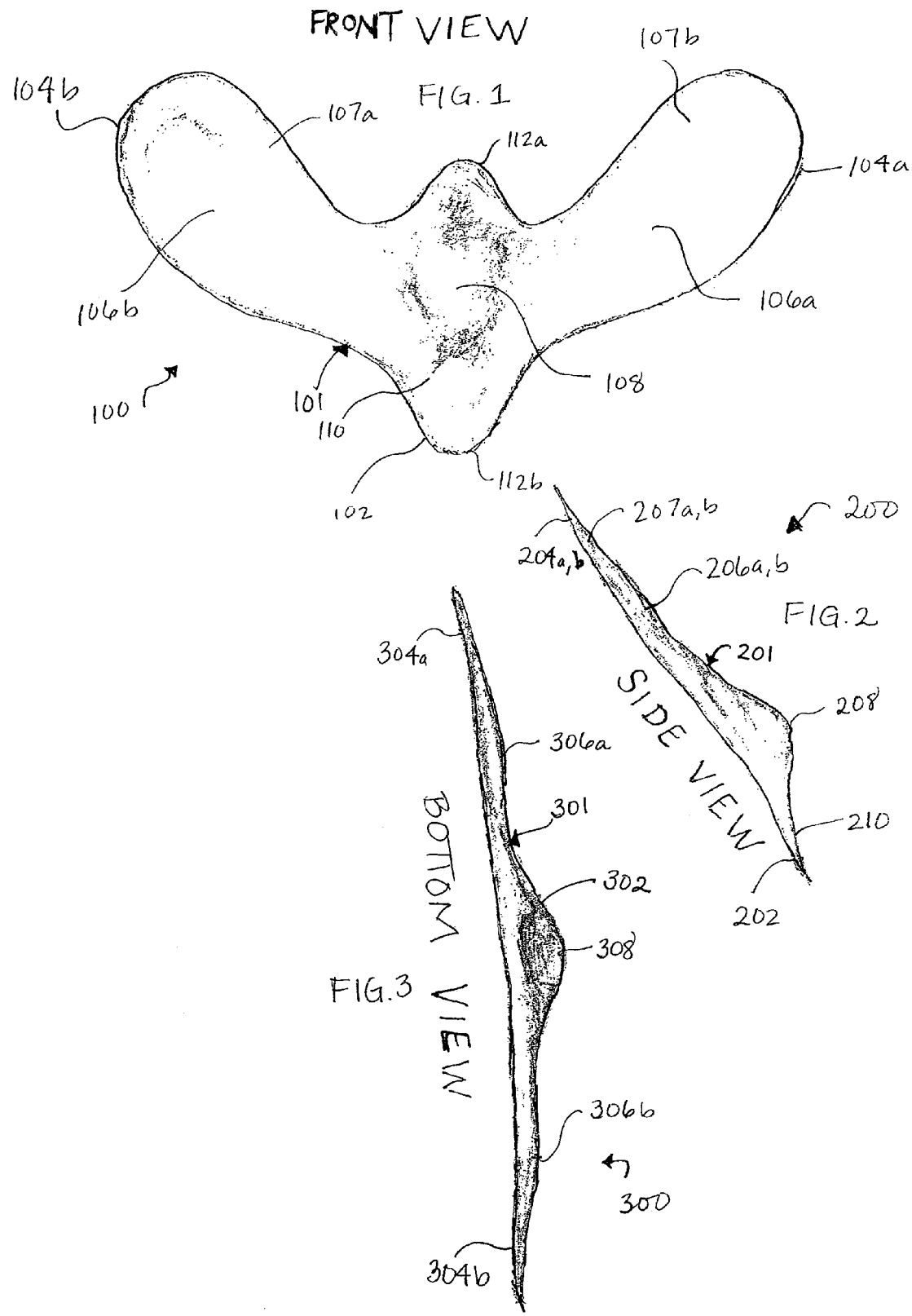

PERSPECTIVE VIEW

PERSPECTIVE VIEW

FRONT VIEW

FRONT VIEW

SIDE VIEW

BOTTOM VIEW

FRONT VIEW

BACK VIEW

TOP VIEW

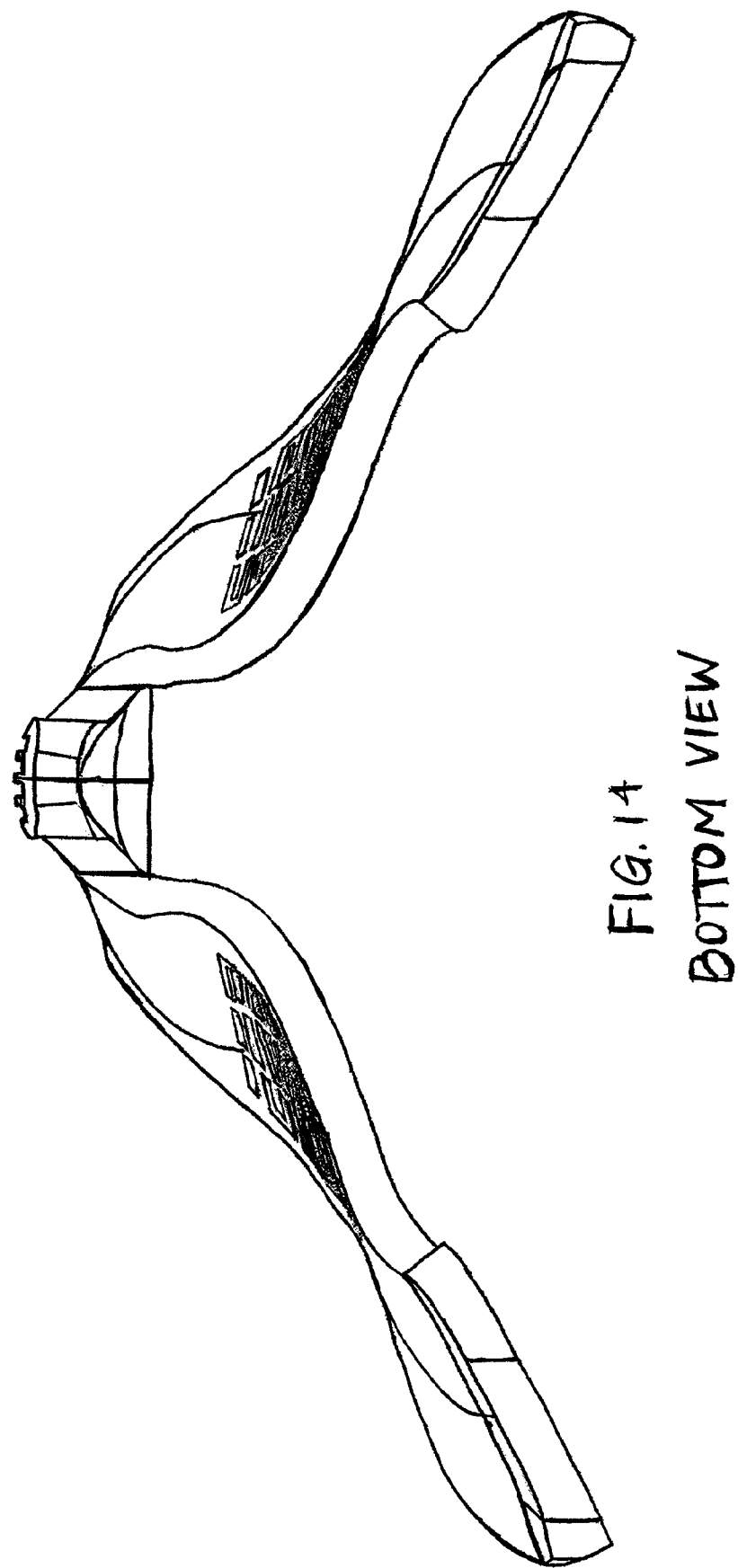
FIG. 14 BOTTOM VIEW

APPARATUS AND METHOD FOR CUSHIONING A VENTILATION MASK

CROSS-REFERENCE TO RELATED APPLICATIONS

This application claims priority to the co-pending U.S. Provisional Application having Ser. No. 61/034,597, filed on Mar. 7, 2008, which is incorporated herein by reference in its entirety.

TECHNICAL FIELD

The present disclosure is generally related to medical technology and, more particularly, is related to an apparatus and method for a cushioning a ventilation mask.

BACKGROUND

Non-invasive ventilation masks (also referred to as ventilation masks) are commonly used in medical treatment to provide breathable gases to a patient. For example, ventilation masks can be used in the treatment of respiratory conditions and sleep disorders (e.g. obstructive sleep apnea) by delivering a flow of breathable gas for, or to assist patient respiration. These ventilation masks typically receive a gas supply line which delivers gas into a chamber formed by the walls of the ventilation mask. The ventilation mask also has a face contacting portion so that the chamber covers the nose and mouth of the patient. The ventilation mask can be secured to the patient's head by straps. The straps can be adjusted to pull the ventilation mask against the face with sufficient force to achieve an airtight seal between the ventilation mask and the patient's face. Because of the sealing effect that is created, gases can be provided at a positive pressure within the ventilation mask for consumption by the patient. Since the ventilation mask is placed on the patient's face with sufficient force to achieve a seal, this can result in excessive pressure on the patient's face.

The pressure may also be excessive because the ventilation mask is improperly or poorly fitted to the patient's face, which can cause various facial wounds. For example, poorly fitting ventilation masks can decrease perfusion, which is the process of nutritive delivery of arterial blood to a capillary bed in biological tissue. Poorly fitting ventilation masks can also cause nasal and facial necrosis, which is the accidental death of cells and living tissue. Furthermore, the ventilation masks may irritate a user's nose bridge, which typically is an area of thin skin, where even slight pressure can cause a blood flow constriction, and, thus, skin breakdown, ulcers, sores, bruising or discomfort. Not only does the patient receive facial wounds, the patient may also experience discomfort due to excessive pressure on the nasal bones, cheekbones and paranasal sinuses.

Also, in addition to the problems caused by poorly fitting ventilation masks, facial wounds and discomfort can also occur if the pressure settings are high on the machine which provides the ventilation to the ventilation mask. Sometimes patients are so dependent on receiving ventilation from a ventilation mask that the patients cannot take breaks from wearing the ventilation mask. In these situations, the facial wounds can be quite severe, particularly when the patient must receive ventilation for a long period of time.

Ventilation mask technology has improved over the years. For example, the U.S. Patent Application Publication No. 2007/0163594 to Ho et al. discloses a cushion for use with a patient interface apparatus that generally conforms to the interface apparatus on one side thereof and on the other side thereof, where contact is made with the patient's face, a chamber having a dampening medium therein for reducing the pressure of the ventilation mask on the patient's face. The chamber is equipped with an orifice that allows the passage of the dampening medium into or out of the chamber in order to adjust the compressive contact with the patient's face.

Additionally, the U.S. Patent Application Publication No. 2007/0125384 to Zollinger et al. discloses a nasal interface ventilation mask for an infant. The apparatus is generally triangular shaped and includes a ventilation mask body and a base. The ventilation mask body forms a cavity for placement over a patient's nose. The portion of the ventilation mask that contacts the face includes a bellows segment characterized by an increased flexibility to thereby lessen the pressure applied by the ventilation mask.

Also, the U.S. Patent Application Publication No. 2007/0125385 to Ho et al. discloses a full face respiratory ventilation mask with an integrated nasal interface. The apparatus provides a patient interface that includes a face plate and a seal member coupled to the face plate. The seal member contacts the user's face to provide a seal interface with the user. The seal member includes an oral cushion portion and a nasal interface portion. The oral cushion portion provides a seal interface with the user over a sealing area that at least partially surrounds the user's mouth. The nasal interface portion is integral with the oral cushion and contacts at least a portion of the user's nose below the bridge of the nose. The apparatus is shown in use in FIG. 27 wherein it can be seen that the top of the apparatus has inserts which protrude into the patient's nostrils while the remainder of the ventilation mask surrounds the patient's mouth. The seal member is typically filled with silicone.

The U.S. Patent Application Publication No. 2007/0107735 to Kwok et al. discloses an apparatus designed to contact a patient's face between the base of the nose and top lip and extend upwardly therefrom to completely encircle the patient's nose. The apparatus is shown in use in FIG. 7. The ventilation mask is designed to seal to the patient's face and to restrict movement between the ventilation mask and the face to maintain the seal via the application of pressure.

Furthermore, the U.S. Patent Application Publication No. 2006/0076019 to Ho et al. discloses a user interface having a pivotable coupling. The apparatus is shown in use in FIG. 7. The patient interface includes a cushion, a shell, and a coupling that are connected together. The cushion has a cavity and the shell has an opening that is connected to the coupling which in turn is connected to a gas delivery conduit. The apparatus extends from the portion of the face between the lower portion of the nose and the lip upwardly to a contact point with the user's forehead. The design of the apparatus allows pivotable couplings to be used and provides for two flex points, one at the user's forehead and another at the user's nose for preventing tangling between the coupling and items connected thereto. The cushion appears to be relatively conventional in design and it is stated that it can be made from a variety of suitable materials such as silicon or foam.

Finally, the U.S. Pat. No. 5,909,732 issued to Diesel et al. discloses a ventilation mask insert designed to provide conformal support for the reflective seal of an oxygen ventilation mask. The insert consists of a formed foam rim which conforms to the contour of the reflective seal and is held in place beneath the reflective seal by a supporting formed framework which conforms to the contours of the interior surface of the ventilation mask face piece. Previously, the unsupported reflective silicon rubber seal was not supported which had the potential for leaks. The insert appears to be primarily designed for use by pilots, life support technicians or those in professions which may require the use of a gas ventilation mask. The cushioned edge is provided by a foam material and fits over the bridge of the user's nose and extends to the chin.

While ventilation mask technology has improved over the years, patients continue to acquire facial wounds and suffer discomfort from the use of ventilation masks.

SUMMARY

Embodiments of apparatuses and methods for preventing facial wounds are provided. For example, the apparatus includes a cushion formed in an inverted "V" shape, wherein the cushion comprises a superior portion and two inferior portions, wherein the superior portion corresponds to the vertex of the inverted "V" shape, wherein the superior portion is configured to cushion the nose of a human, and wherein the two inferior portions are configured to cushion the cheekbones of a human.

Other systems, methods, features, and advantages of the present disclosure will be or will become apparent to one with skill in the art upon examination of the following drawings and detailed description. It is intended that all such additional systems, methods, features, and advantages be included within this description, and be within the scope of the present disclosure.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

FIG. 1 is a front view of a first embodiment of an apparatus for preventing facial wounds.

FIG. 2 is a side view of the first embodiment illustrated in FIG. 1.

FIG. 3 is a bottom view of the first embodiment illustrated in FIGS. 1 and/or 2.

FIG. 14 is a bottom view of the fourth embodiment illustrated in FIG. 10.

DETAILED DESCRIPTION

Figure 4:
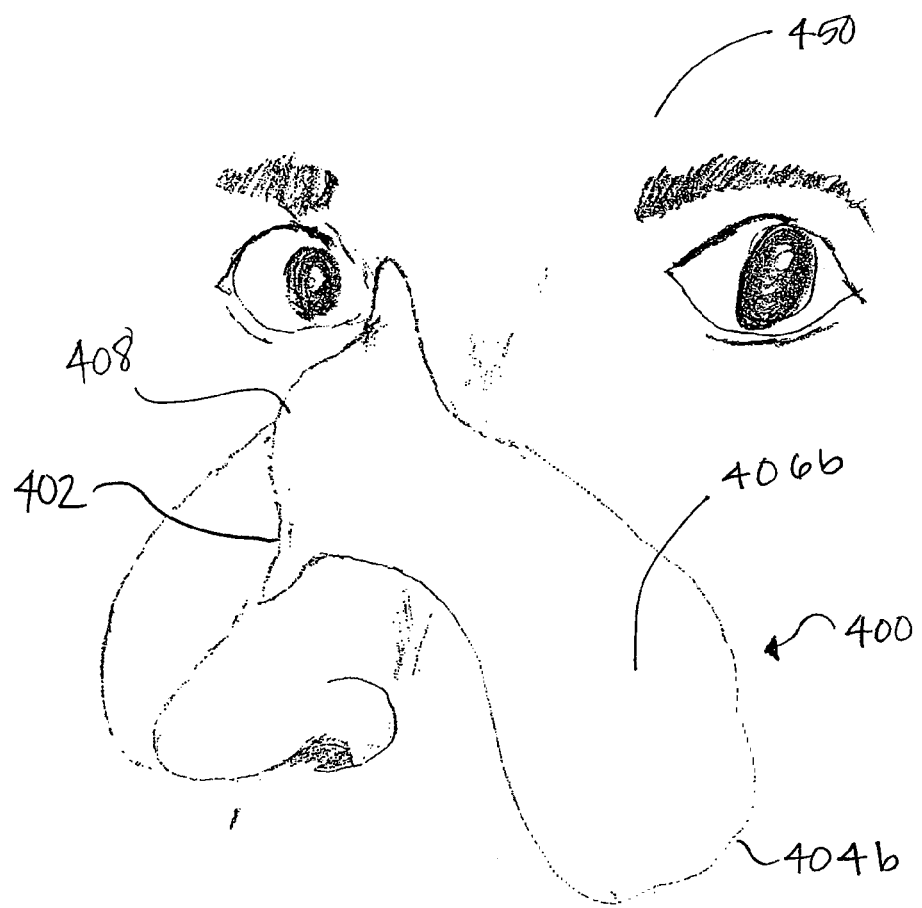
FIG. 4 is a perspective view of the first embodiment placed on a patient.

FIG. 1 illustrates a first embodiment of an apparatus for preventing facial wounds due to the use of a ventilation mask (e.g., a ventilation mask and/or NIV ventilation mask). In this embodiment, the apparatus 100 includes a cushion 101 formed in the shape of a "V," and the cushion 101 is dimensioned to fit over a patient's nose and cheeks. When in use, the apparatus 100 behaves as an interface, cushion and/or buffer for the ventilation mask. However, the apparatus 100 does not completely cover the patient's nostrils or nares when the apparatus 100 is placed on the patient's face. This way, the patient may still admit and expel the ventilated gases for respiration.

The cushion 101 may be made of a cushioning material that is soft and pliable. In one embodiment, the cushion 101 is made of silicone, but other cushioning materials, such as a hydrocolloid material, could be used as well In addition, the cushioning material may include an injectable gel such as a silicone elastomer, medical grade gel, foam rubber, and/or one of a variety of cushioning materials. In some embodiments, the cushioning material is a breathable material. In some embodiments, the cushioning material is made of a combination of the previously mentioned materials.

The cushion 101 helps alleviate, distribute and dampen the pressure applied to the patient's face by the Ventilation mask. When in use, the cushion 101 may absorb and distribute some of the force applied by the ventilation mask and result in less force applied directly to the patient's nose and cheeks. This means that less force may be applied to the cartilage bridge and nasal bones associated with the nose. Likewise, less force may be applied to the cheekbones. In addition, because less force may be applied to those areas, less force is also applied to the patient's paranasal sinuses, such as the sphenoid sinuses and maxillary sinuses.

Also, because the cushion 101 may absorb the pressure applied by the ventilation mask, the cushioning material may spread or expand. This spreading or expansion may result in an increase in the surface area of the pressure applied to the patient's face. Thus, since the pressure may be better distributed across the face, the patient may develop fewer sores.

As illustrated in FIG. 1, the apparatus 100 includes a cushion 101, which may include a superior portion 102 and two inferior portions 104a,b. The superior portion 102 may correspond to a patient's nose, and the two inferior portions 104a,b may correspond to a patient's cheeks. In some embodiments, the superior portion 102 may be shaped to conform to the contours of a patient's nose, and the two inferior portions 104a,b may be shaped to conform to the contours of a patient's cheeks.

In some embodiments, the thickness of the cushion 101 corresponds to the boniest regions of a patient's face. In other words, the thickness of the cushion 101 corresponds to the bone structure of a human face and has a pillow-like shape. As shown in FIG. 1, each inferior inner region 106a,b of the inferior portions 104a,b may be thicker than the inferior outer region 107a,b of each inferior portion 104a,b. The inferior inner regions 106a,b, may correspond to a patient's cheekbones. Similarly, the superior inner region 108 may be thicker than the superior outer region 110 of the superior portion 102. This thicker superior inner region 108 may correspond to the cartilage and nasal bones of a patient's nose.

This correspondence of thickness to the boniest regions of a patient's face is also illustrated in FIGS. 2 and 3. FIG. 2 depicts a side view of the apparatus 200, which shows the cushion 201 including the superior inner region 208 of the superior portion 202 as being thicker than the superior outer region 210. The thicker superior inner region 208 may be thickest in the region of the superior portion 202 that would typically lie over the cartilage of a patient's nose. Similarly, the two inferior inner regions 206a,b would each be thickest in the region of the inferior portions 204a,b that would typically lie on a patient's cheekbones.

FIG. 4 is a perspective view of the first embodiment of the apparatus 400 placed on the face of a patient. Specifically, the apparatus 400 may be placed on the patient's nose 491 and cheeks 492a,b. Also, FIG. 4 further illustrates the correspondence of the thickness of the apparatus 400 to the boniest regions of a patient's face. For example, the inferior portion 404b is placed over the patient's cheek, and the inferior inner region 406b, which is thick, corresponds to the patient's cheekbone. Further, the superior inner region 408 of the superior portion 402 corresponds to the bones and cartilage in the patient's nose. The thicker cushioning material allows for the shift of pressure from being concentrated at certain pressure points to being better distributed across the patient's face, to allow for enhanced blood flow to poorly perfused and bony structure areas where the ventilation mask is applied.

In some embodiments, the cushioning material may also be flexible. Silicone is an example of a cushioning material that is also flexible. The use of a flexible material may allow the apparatus to adapt to a patient's face to help create airtight seal. The adaptation to a patient's face may also help provide at least some cushioning on the areas of the patient's face covered by the apparatus and a ventilation mask.

Figure 5:
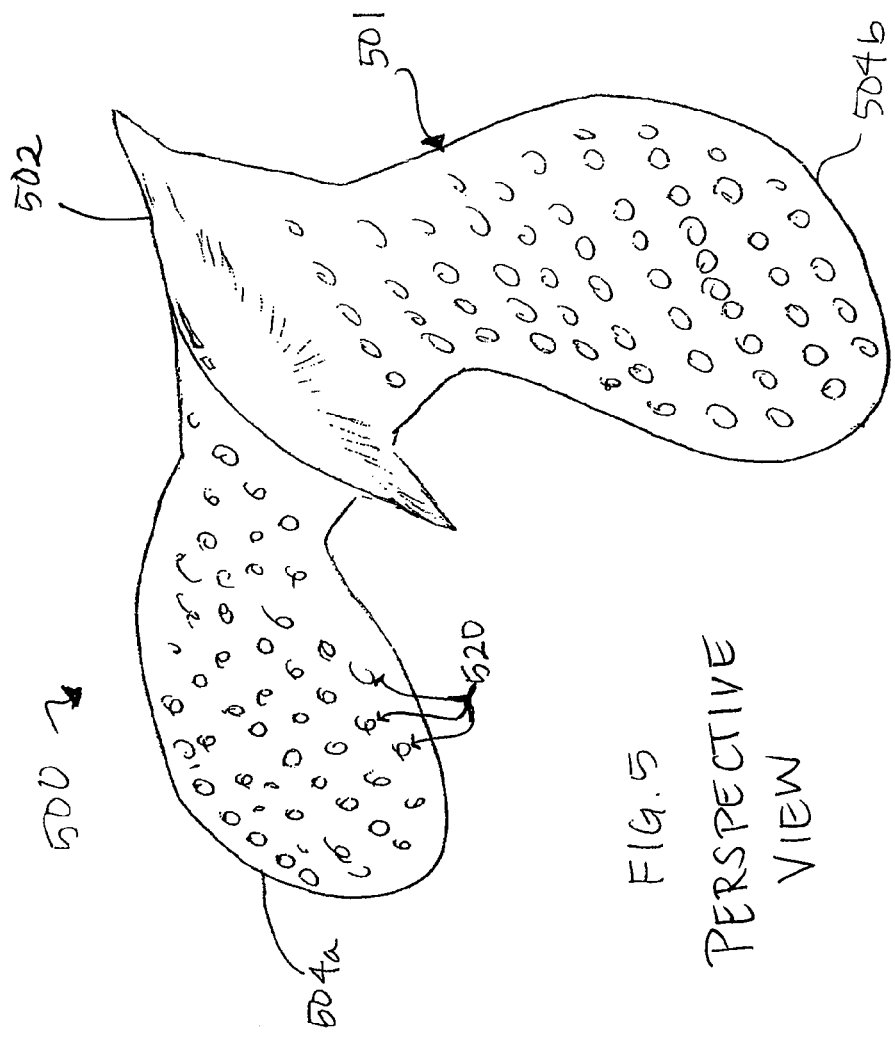
FIG. 5 is a perspective view of a second embodiment of the apparatus including pores.

FIG. 5 is a perspective view of a second embodiment of an apparatus for preventing facial wounds. Specifically, the apparatus 500 may include pores 520 in the cushion 501 as shown in FIG. 5. These pores 520 may be small holes that span the thickness of the cushion 501. In some embodiments, the pores 520 may merely be distributed in the inferior portions 504a,b, as shown in FIG. 5, or merely in the superior portion. Alternatively, these pores can be distributed throughout the apparatus including both the inferior portions and superior portion. The pores may allow a patient's skin to breathe and/or help the apparatus to absorb and distribute pressure applied by the ventilation mask.

Figure 6:
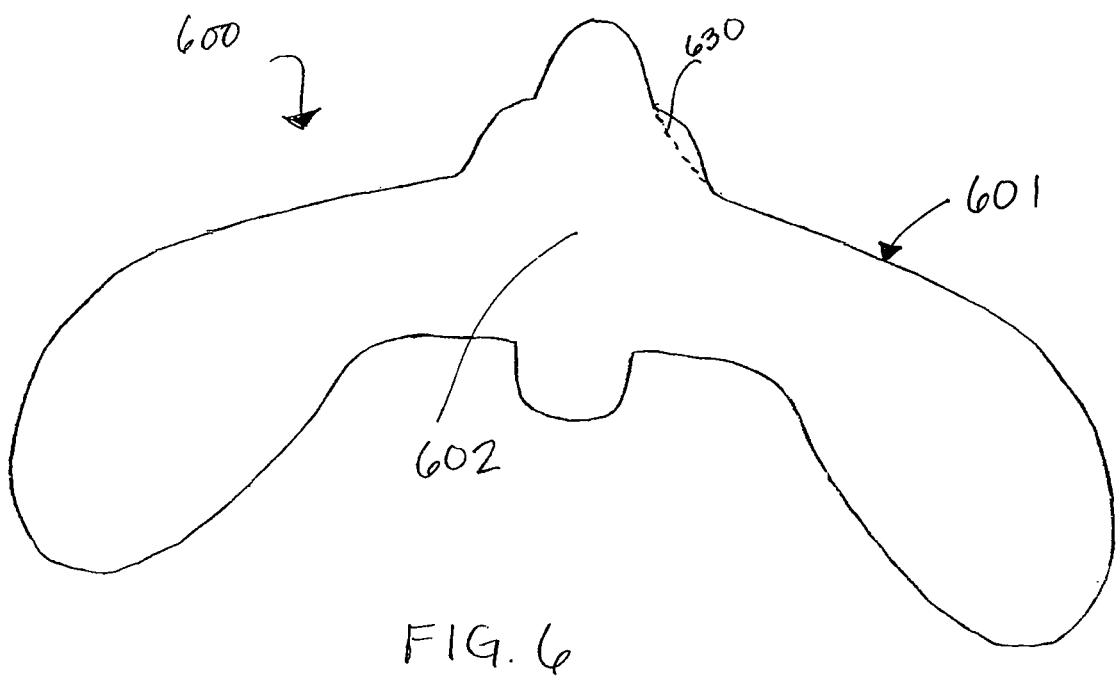
FIG. 6 is a front view of a third embodiment of the apparatus including a perforation.

In some embodiments, the apparatus may be trimmed to accommodate a patient with a smaller face or to accommodate a patient's special needs. The trimming may be accomplished with scissors, a knife or one of a variety of cutting devices. Alternatively, the edges of the apparatus may be perforated, allowing an edge to be quickly torn from the apparatus in order to adjust the size or shape of the apparatus. FIG. 6 illustrates an example of an apparatus 600 including a perforation 630 for modifying the shape of the superior portion 602 of the apparatus 600. In other embodiments, the apparatus may have multiple perforations so that various sizes could be chosen from one original apparatus. Also, the apparatus can be made in various sizes such as large, medium and small sizes instead of including a perforation.

Also, in some embodiments, the apparatus for preventing facial wounds includes lips. These lips aid in easy removal of the apparatus and easy positioning on the patient's face. For example, FIG. 1 illustrates these lips 112a,b on the cushion 101 at the superior portion 102.

Figure 7:
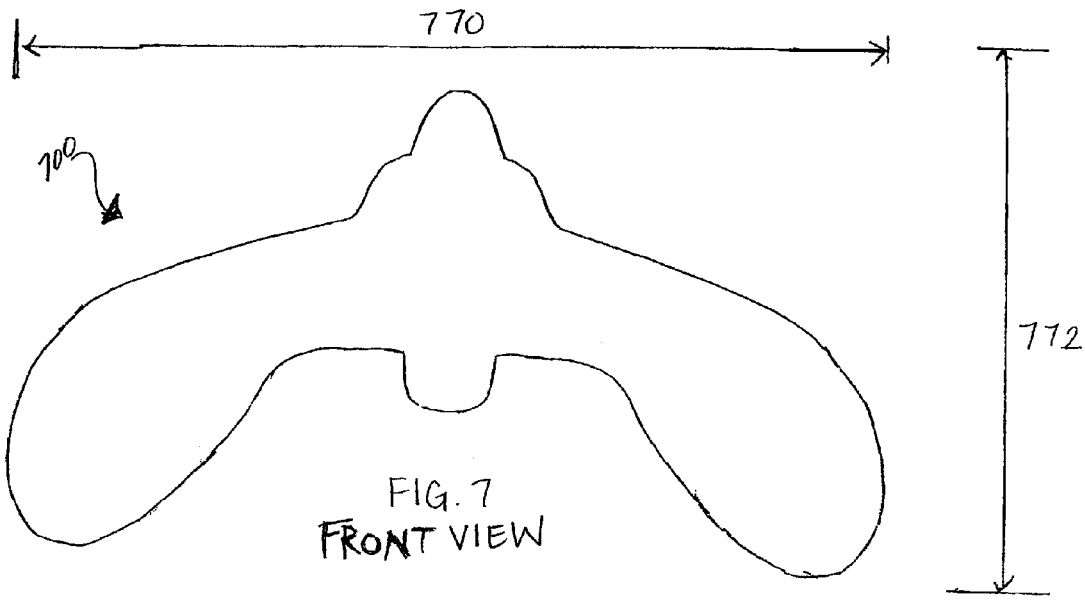
FIG. 7 is a front view showing dimensions of a third embodiment of the apparatus.
Figure 8:
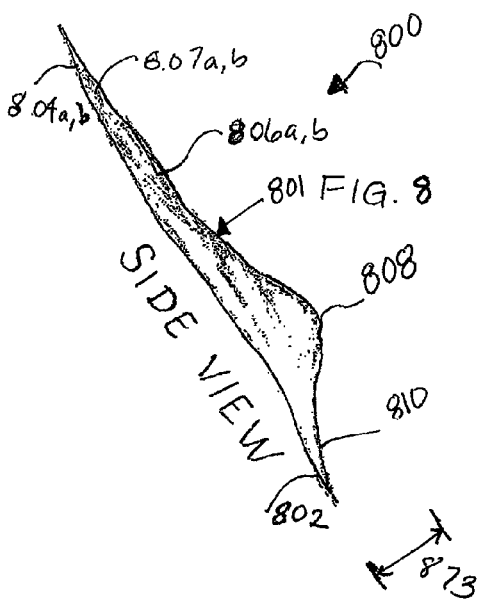
FIG. 8 is a side view showing an elevational dimension of a third embodiment of the apparatus.
Figure 9:
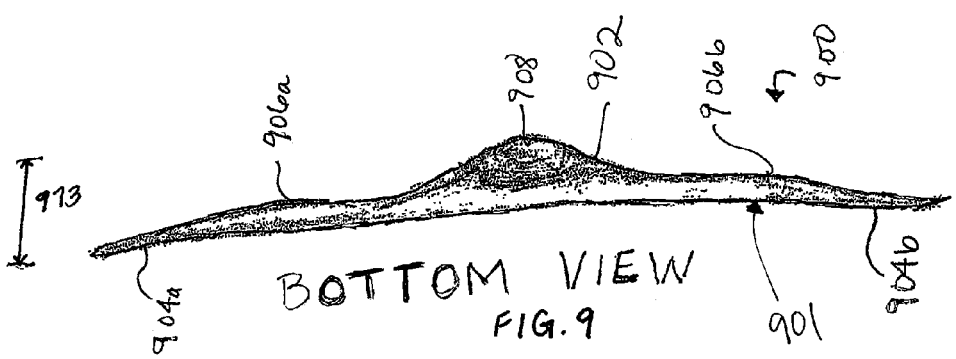
FIG. 9 is a bottom view showing an elevational dimension of the third embodiment of the apparatus.
Figure 10:
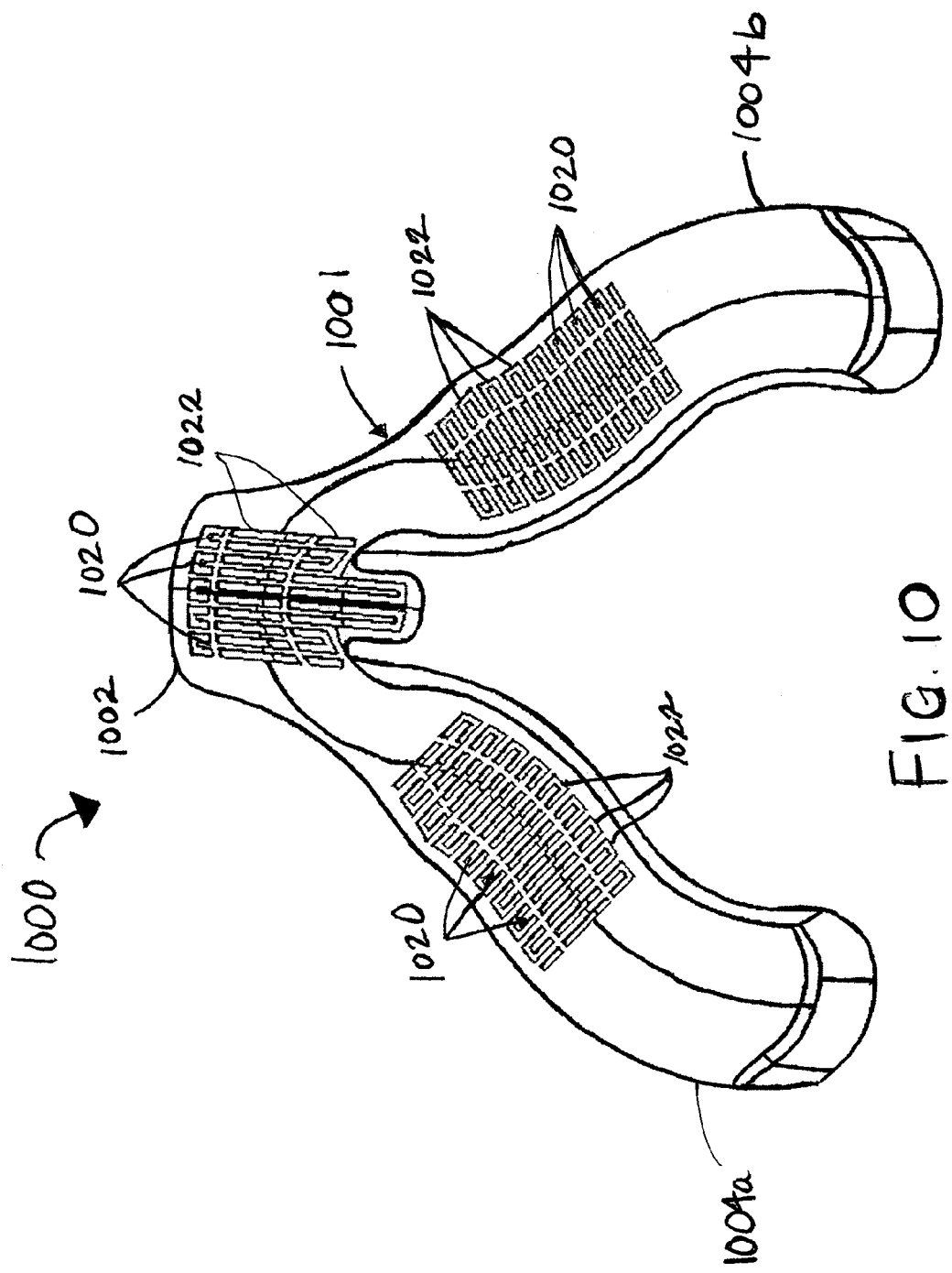
FIG. 10 is a front view of a fourth embodiment of the apparatus including a plurality of ribs.
Figure 11:
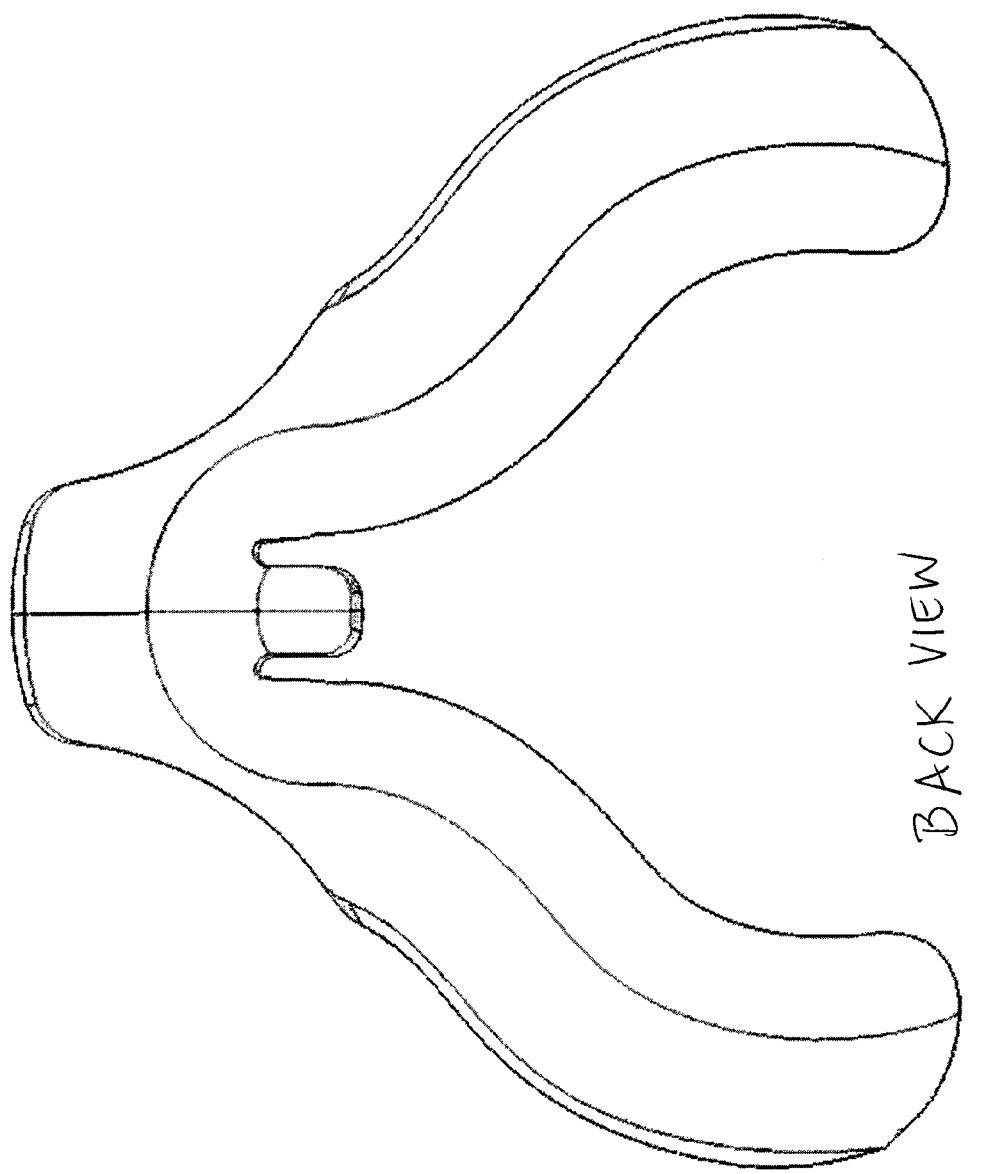
FIG. 11 is a back view of the fourth embodiment illustrated in FIG. 10.
Figure 12:
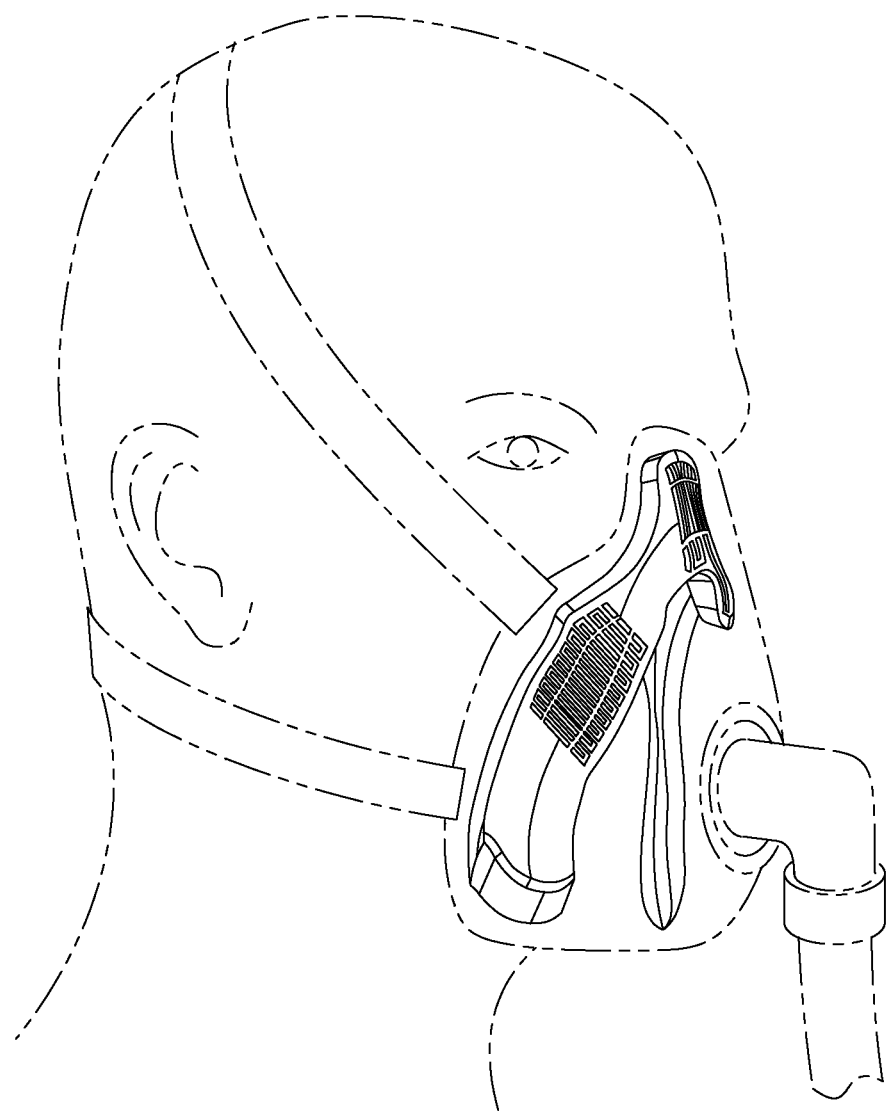
FIG. 12 is a side view of the fourth embodiment illustrated in FIG. 10.
Figure 13:
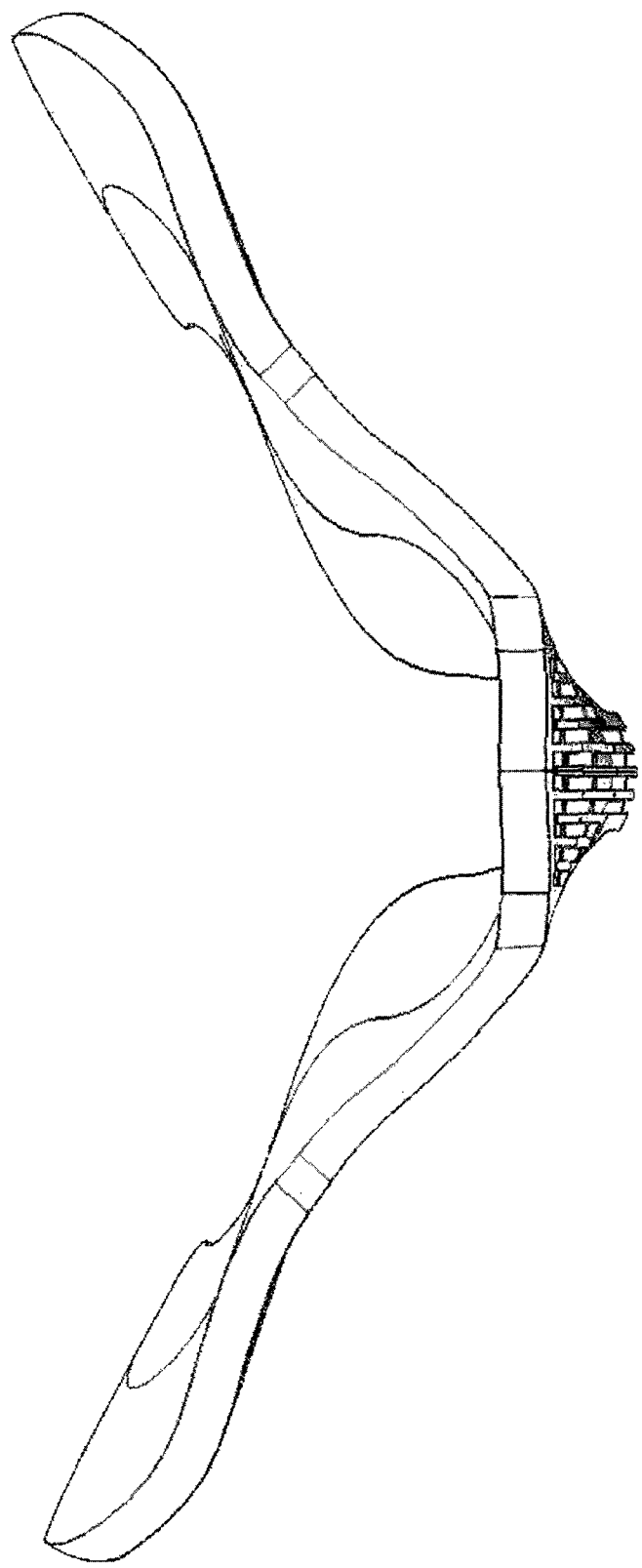
FIG. 13 is a top view of the fourth embodiment illustrated in FIG. 10.

FIGS. 7, 8 and 9 illustrate a nonlimiting example of the dimensions of a third embodiment of the apparatus 700. In FIG. 7, the length 770 of the cushion 701 may be six inches, and the width 772 of the cushion 701 may be five inches. FIGS. 8 and 9 illustrate elevational views of the apparatus 800, 900 and show the elevation 873, 973 as being approximately two inches. Other dimensions and sizes of the apparatus may be used instead. The cushion 701 may be dimensioned to accommodate a ventilation mask.

FIGS. 10-14 illustrate a fourth embodiment of the apparatus including a plurality of ribs. The cushion 1001 is shown beneath a ventilation mask 1203 worn by a patient 1201. These ribs aid in cushioning, relieving pressure and absorbing shock. Specifically, as illustrated in the front view in FIG. 10, the cushion 1001 of the apparatus 1000 includes ribs 1020 corresponding to openings 1022. In the embodiment illustrated in FIGS. 10-14, the openings 1022 do not span the thickness of the cushion 1001, as can be specifically seen in the back view illustrated FIG. 11. In other embodiments, the openings 1022 may span the thickness of the cushion 1001. Further, in the embodiments illustrated in FIGS. 10-14, the ribs 1020 and openings 1022 are placed in certain regions of the superior portion 1002 and the two inferior portions 1004a, b. In other embodiments, the ribs 1020 and openings 1022 are placed throughout the cushion 1001 instead of only being placed in certain regions. The openings 1022 may allow a patient's skin to breathe while the ribs 1020 help the apparatus to absorb and distribute pressure applied by the ventilation mask.

Also, in the fourth embodiment illustrated in FIGS. 10-14, the thickness of the cushion is uniform as opposed to having the thickness of the cushion correspond to the bone structure of a patient's face, as illustrated in the nonlimiting examples in FIGS. 1-4 and 8-9. However, in some embodiments, the apparatus may include ribs, openings and a thickness of the cushion that corresponds to the bone structure of a patient's face.

In some embodiments, the apparatus is attachable to the ventilation mask. The apparatus could be attached to the ventilation mask by an attachment means such as, for example, adhesion, a snap closure, Velcro™, and/or glue. The apparatus may, be coupled to the ventilation mask instead of directly abutting the ventilation mask. Also, in some embodiments, the apparatus includes a skin-safe adhesive for securing the apparatus to a patient's face.

In some embodiments, a coating of medicine can be applied to the surface of the cushion that will touch the patient's face. In this way, when the apparatus is placed on the patient's face, medicine can be delivered to the patient's existing facial wounds, such as facial sores. One of a variety of medications may be applied to the apparatus as a coating. For example, the medication might be a vasodilator such as Xenoderm™ or a topical antibiotic ointment such as Neosporin™.

In addition to the various embodiments of an apparatus described above, methods are provided for cushioning a ventilation mask. In one embodiment, the method includes a step of applying a "V" shaped cushion to a patient's nasal bones, nasal cartilage and cheekbones. This cushion may be made of a cushioning material, which may be silicone or one or more of a variety of cushioning materials. The method also may include applying a ventilation mask over the applied "V" shaped cushion. Further, the method may include creating a substantially airtight seal between the patient's face and the ventilation mask using the "V" shaped cushion. In addition, the method may include distributing a pressure applied to the nose and cheekbones of the patient by the applied ventilation mask using the applied "V" shaped cushion.

In still another embodiment, the method includes a step of applying a cushioning apparatus to a patient's nasal bones, nasal cartilage and cheekbones. This cushioning apparatus is made of a cushioning material, which may be silicone or one or more of a variety of cushioning materials. The method also includes a step of placing a ventilation mask over the applied cushioning material. The method further includes shifting or distributing the pressure applied by the ventilation mask. In this way, the pressure may be less intense at certain pressure points such as the bonier regions of the patient's face, and the pressure may be better distributed across the patient's face.

It should be emphasized that the above-described embodiments of the present disclosure are merely possible examples of implementations, merely set forth for a clear understanding of the principles of the disclosure. Many variations and modifications may be made to the above-described embodiment(s) of the disclosure without departing substantially from the spirit and principles of the disclosure. All such modifications and variations are intended to be included herein within the scope of this disclosure and the present disclosure and protected by the following claims.

The invention claimed is:

1. An apparatus for preventing facial wounds caused by an applied ventilation mask, comprising:
   a ventilation mask for providing breathable gases to a patient,
   a single piece, same-molded, cushion formed in an inverted "V" shape in which the lower portion of the inverted "V" is open, and including a plurality of ribs for cushioning, relieving pressure, and absorbing shock applied to said cushion by said ventilation mask,
   wherein the cushion comprises a superior portion and two inferior portions,
   wherein the superior portion corresponds to the vertex of the inverted "V" shape and has increased thickness to cushion the bridge of a wearer's nose,
   wherein the superior portion is sized and shaped to contact the nose of a human while the two inferior portions are sized and shaped to respectively contact the cheekbones of the human such that the superior portion cushions the nose from the ventilation mask and the two inferior portions cushion the respective cheekbones from the ventilation mask.

2. The apparatus of claim 1, wherein the cushion is sized and shaped to be thicker where the cushion contacts a pressure point of the face of the human.

3. The apparatus of claim 1, wherein the superior portion is thicker than at least one of the two inferior portions.

4. The apparatus of claim 1, wherein the cushion includes a cushioning material selected from the group consisting of: silicone and a hydrocolloid material.

5. The apparatus of claim 1, wherein the cushioning material is a flexible material.

6. The apparatus of claim 1, wherein the cushion includes a cushioning material including an injectable gel selected from the group consisting of: a silicone elastomer, medical grade gel, and foam rubber.

7. The apparatus of claim 1, wherein the cushion is operative to redistribute pressure applied by a ventilation mask away from a pressure point.

8. The apparatus of claim 1, wherein the cushion is dimensioned to accommodate the ventilation mask.

9. The apparatus of claim 1, further comprising a medication coating applied to a surface of the cushion.

10. The apparatus of claim 9, wherein the medication coating is selected from the group consisting of: a vasodilator and an antibiotic ointment.

11. The apparatus of claim 1, wherein the cushion includes a perforation.

12. The apparatus of claim 1, wherein the cushion includes a plurality of pores.

13. The apparatus of claim 1, wherein the cushion further defines openings adjacent to the ribs.

14. The apparatus of claim 13 in which said cushion has a thickness and said openings extend through a portion of said thickness.

15. The apparatus of claim 13 in which said cushion has a thickness and said openings extend through said thickness.

16. The apparatus of claim 1, wherein the superior portion includes a lip protruding from the superior portion.

17. The apparatus of claim 1, further including an attachment means for attaching the cushion to the ventilation mask.

* * * * *